(12) United States Patent
Gozlan et al.

(10) Patent No.: US 9,499,559 B2
(45) Date of Patent: Nov. 22, 2016

(54) METHOD FOR PREPARING LONG-CHAIN ALKYL CYCLIC ACETALS MADE FROM SUGARS

(71) Applicants: SYRAL BELGIUM NV, Aalst (BE); UNIVERSITÉ CLAUDE BERNARD LYON 1, Villeurbanne (FR); CENTRE NATIONAL DE LA RECHERCHE SCIENTIFIQUE (C.N.R.S.), Paris (FR)

(72) Inventors: Charlotte Gozlan, Villeurbanne (FR); Nicolas Duguet, Villeurbanne (FR); Marc Lemaire, Villeurbanne (FR); Yves Queneau, Villeurbanne (FR); Andreas Redl, Aalst (BE)

(73) Assignees: SYRAL BELGIUM NV, Aalst (BE); UNIVERSITÉ CLAUDE BERNARD LYON 1, Villeurbanne (FR); CENTRE NATIONAL DE LA RECHERCHE SCIENTIFIQUE (C.N.R.S.), Paris (FR)

( * ) Notice: Subject to any disclaimer, the term of this patent is extended or adjusted under 35 U.S.C. 154(b) by 0 days.

(21) Appl. No.: 14/898,475

(22) PCT Filed: Jun. 13, 2014

(86) PCT No.: PCT/IB2014/062194
§ 371 (c)(1),
(2) Date: Dec. 14, 2015

(87) PCT Pub. No.: WO2014/199345
PCT Pub. Date: Dec. 18, 2014

(65) Prior Publication Data
US 2016/0130277 A1 May 12, 2016

(30) Foreign Application Priority Data

Jun. 14, 2013 (FR) ..................................... 13 01375

(51) Int. Cl.
*C07D 493/04* (2006.01)
*C07D 407/04* (2006.01)

(52) U.S. Cl.
CPC ........... *C07D 493/04* (2013.01); *C07D 407/04* (2013.01)

(58) Field of Classification Search
CPC ....................................................... C07D 493/04
USPC ........................................................ 549/364
See application file for complete search history.

(56) References Cited

U.S. PATENT DOCUMENTS 3,484,459 A * 12/1969 Hartmann ............ C07D 307/20
549/476

* cited by examiner

*Primary Examiner* — Taofiq A Solola
(74) *Attorney, Agent, or Firm* — Symbus Law Group, LLC; Clifford D. Hyra

(57) ABSTRACT

Long-chain alkyl cyclic acetals made from sugars are obtainable by a method that comprises the steps consisting of:
  dehydrating a hexitol in a monoanhydrohexitol substrate;
  reacting the monoanhydrohexitol substrate obtained with an alkyl aldehyde reagent containing 5 to 18 carbon atoms, by means of an acetalization reaction with a substrate/reagent ratio of between 5:1 and 1:1, or with a derivative of an alkyl aldehyde reagent containing 5 to 18 carbon atoms, by means of a transacetalization reaction with a substrate/reagent ratio of between 1:1 and 1:3, in the presence of acid catalyst and in an environment that is free of solvent or that consists of non-aqueous polar solvent;
  collecting the long-chain alkyl acetal of hexitan from the mixture obtained.

8 Claims, 2 Drawing Sheets

METHOD FOR PREPARING LONG-CHAIN ALKYL CYCLIC ACETALS MADE FROM SUGARS

This application claims the benefit of French patent Application No. 13/01375, filed Jun. 14, 2013, which is hereby incorporated by reference in its entirety.

FIELD OF THE INVENTION

The present invention relates to a method for preparing long-chain alkyl cyclic acetals made from sugars.

BACKGROUND

In the scientific and technical literature, sugar-based surfactant molecules are well known. Among them, sucrose fatty acid esters, sorbitan esters and long-chain alkyl polyglucosides have been widely used in foods, personal care, and cosmetic and pharmaceutical applications. Some of these surfactants have also found wide acceptance in household and industrial cleaning applications and as lubricants.

Despite their wide use and acceptance, it is well known that ester-based surfactants are stable only over a limited range of pH, whereas alkyl glucosides are stable under alkaline and neutral conditions but not under acidic conditions.

Other disadvantages are associated with the methods used to obtain these derivatives. In the case of higher alkyl glucosides, transacetalization is necessary. Rather complicated and costly equipment must be used in order to obtain a sufficiently pure product. In the case of sugar-based esters, in particular sorbitan esters, expensive and toxic solvents or high reaction temperatures are required in order to obtain products with sufficiently high yield.

In order to improve the acidic stability of sugar-based surfactant compounds, a sugar alcohol ether was recently proposed in the document WO 2012/148530. This application describes a method for preparing these polyol ethers whereby a molten mass of polyol is reacted with a higher alkyl aldehyde under reductive alkylation conditions. Here again, difficult and extreme conditions are necessary, in combination with high-pressure equipment, in order to carry out the reductive alkylation reaction. In order to obtain the desired products, excess sugar alcohol relative to aldehyde is deemed necessary. This results in high energy consumption per mole of sugar alcohol ether.

Another group of sugar-based surfactant molecules is represented by long-chain alkyl cyclic acetals of sugars, as disclosed in several scientific and technical publications.

In *Carbohydrate Research* (1997) p. 85-92, higher alkyl cyclic acetals of sucrose, and methods for obtaining same, are described. The acetals thus obtained could be of interest in the detergents industry because these products are stable in basic and neutral media, unlike ester derivatives. Moreover, they had advantageous critical micelle concentration (CMC) values. In OPPI Briefs (1998) p. 460-464, an improved method for preparing such sucrose-based compounds was disclosed.

In the document U.S. Pat. No. 6,251,937 (FR2761991) and JAOCS (1994) p. 705-710, higher alkyl cyclic acetals of gluconic acid derivatives having surfactant properties in basic and neutral media are described. At the same time, they also exhibited strong hydrolysis in acidic medium.

In the patent EP 0 019 999, the preparation of higher alkyl cyclic acetals of sugar derivatives, in particular of sorbitol derivatives, is disclosed. Thus proposed is an improved method using acetic acid as reaction medium. This reaction produces a sorbitol alkyl acetal partially substituted with acetate groups. In this same document, reference is made to the U.S. Pat. No. 4,031,112. In the latter document, it is mentioned that the reaction conditions described therein are usable to prepare long-chain alkyl acetals of sorbitol. It was noted, however, as mentioned in the patent EP 0 019 999, that the conditions described cause extensive decomposition of the products and the reagents, whereby the product's yield and quality become commercially unacceptable.

In the U.S. Pat. No. 3,484,459, reference is made to the preparation of cyclic acetals of sorbitan. In this document, mention is made of a wide range of aldehydes and ketones as potential reagents. These acetalization reactions are used to collect residual 1,4-sorbitan from a mixture of hexitans, after separating the pure acetals by fractional distillation. The sorbitan acetal thus obtained is hydrolyzed, and 1,4-sorbitan is collected by crystallization. The acetalization is thus carried out with a large excess of reagent, using long reaction times. The conditions used are relatively unattractive in terms of methodology.

In light of the above, it is clear that the products and/or methods described with regard to higher alkyl cyclic acetals made from sugars show a certain number of gaps. Apart from the polyol ether described in WO 2012/148530, all the other sugar-based surfactant molecules are unstable or are insufficiently stable under acidic conditions, whereas in most cases the methods use solvents or reaction conditions that are not safe from an environmental point of view, and/or that consume a lot of energy and/or are not profitable from an industrial point of view.

Consequently, it is obvious that there remains an unsatisfied need to have sugar-based long-chain alkyl cyclic acetals that exhibit improved stability under acidic conditions, in combination with good emulsifying properties. Moreover, there also remains a need to have methods for preparing these compounds, methods that are acceptable for the environment, advantageous in terms of energy consumption, and easy to implement industrially.

SUMMARY

The object of the invention is obtained by providing a method for preparing a long-chain alkyl cyclic acetal made from sugars, wherein the method comprises the following steps:
   dehydrating a hexitol by forming a monoanhydrohexitol;
   reacting the monoanhydrohexitol substrate obtained with an alkyl aldehyde reagent containing 5 to 18 carbon atoms, by means of an acetalization reaction with a substrate/reagent ratio of between 5:1 and 1:1, or with a derivative of an alkyl aldehyde reagent containing 5 to 18 carbon atoms, by means of a transacetalization reaction with a substrate/reagent ratio of between 1:1 and 1:3, preferably, in the presence of acid catalyst and/or in an environment that is free of solvent or that consists of non-aqueous polar solvent;
   collecting the long-chain alkyl acetal of hexitan from the mixture obtained.

Typically, by "long-chain alkyl" is understood an alkyl radical comprising preferably 5 to 18 carbon atoms, preferably 8 to 12 carbon atoms.

In a preferred method according to the invention, said hexitol is selected from the group consisting of: sorbitol, mannitol, galactitol and iditol. Sorbitol is the preferred hexitol.

In a more preferred method of the invention, said alkyl aldehyde reagent contains 8 to 12 carbon atoms.

The acetalization reaction with an aldehyde reagent is executable with or without solvent. When solvent is used, and according to an advantageous method according to the invention, said non-aqueous polar solvent is selected from the group consisting of: DMF, DMSO, DMA, acetonitrile, THF, methyl THF and ethyl acetate.

In a particular method in accordance with the invention, said long-chain alkyl acetal of hexitan is collected by separation.

In a preferred method according to the invention, said monoanhydrohexitol substrate is purified 1,4-sorbitan.

In a method more particularly according to the invention, said long-chain alkyl acetal of hexitan is composed of four diastereoisomers.

BRIEF DESCRIPTION OF THE DRAWINGS

This invention will now be described in further detail and illustrated by graphs and examples which should be regarded as not limiting the scope of the invention as such and as expressed in the following claims below, wherein the reference numbers are used to indicate the appended drawings wherein:

DETAILED DESCRIPTION

According to this invention, it was noted, surprisingly, that long-chain alkyl cyclic acetals made from sugar are obtainable by a method comprising the following steps:
dehydrating a hexitol in a monoanhydrohexitol,
reacting the monoanhydrohexitol substrate obtained with an alkyl aldehyde reagent containing 5 to 18 carbon atoms, by means of an acetalization reaction with a substrate/reagent ratio of between 5:1 and 1:1, or with a derivative of an alkyl aldehyde reagent containing 5 to 18 carbon atoms, by means of a transacetalization reaction with a substrate/reagent ratio of between 1:1 and 1:3, in the presence of acid catalyst and in an environment that is free of solvent or that consists of non-aqueous polar solvent,
and collecting the long-chain alkyl acetal of hexitan from the mixture obtained.

Typical hexitols are sorbitol, mannitol, galactitol and iditol, whereby sorbitol is by far the most plentiful.

The formation of monoanhydrosorbitol has already been described in several publications. Thus, various methods for obtaining this intermediate compound have been described.

In an embodiment, sorbitol is dissolved in water in the presence of acid catalyst and heated under atmospheric conditions for a period of time sufficient to obtain the maximum 1,4-sorbitan content. Such a method is described in Acta Chemical Scandinavica B (1981) p. 441-449. Methods where the reaction is carried out under reduced pressure (U.S. Pat. No. 2,390,395 and US 2007173651) or under moderate hydrogen pressure (US2007173654) have also been disclosed. In this patent application US2007173654 a noble metal co-catalyst is used, which leads to rather high concentrations of isosorbide, in the place of 1,4-sorbitan.

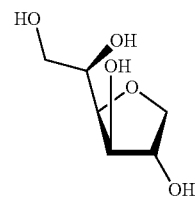

1,4-Sorbitan

According to the current patent application, it was noted that according to a preferred embodiment the intermediate product 1,4-sorbitan was obtainable with good yield by treating a molten mass of sorbitol with solid acid catalyst in a hydrogen atmosphere at a pressure of 20 to 50 bar, this at a reaction temperature that is variable between 120 and 170° C., for a period of time sufficient to obtain an optimal yield of sorbitan. The preferred reaction temperatures are between 130 and 140° C.

Figure 1:
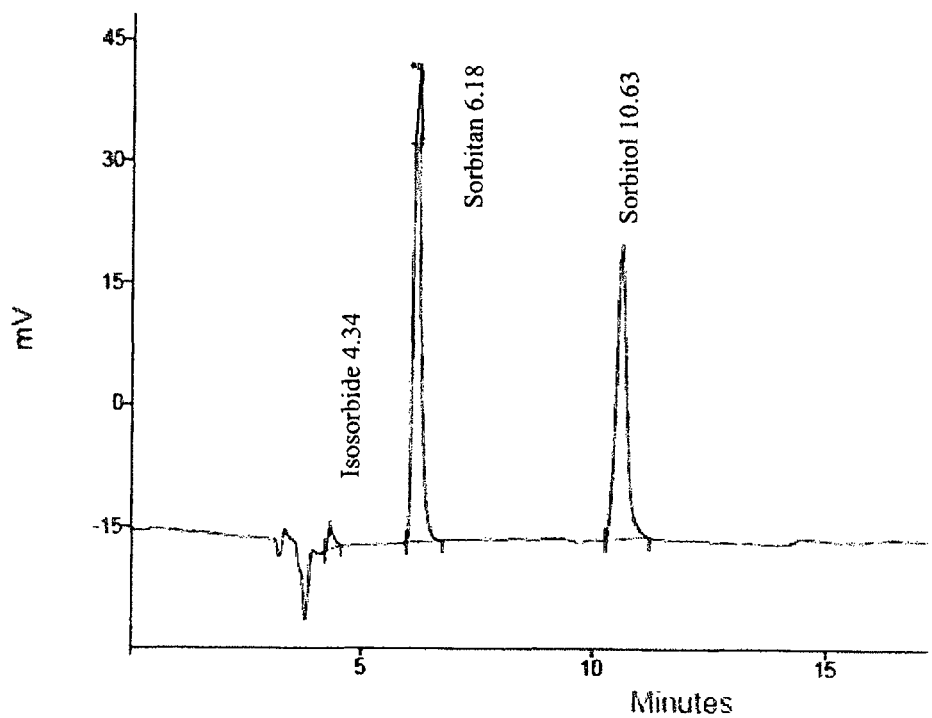
FIG. 1: represents a chromatogram of the reaction mixture obtained during the dehydration reaction.

The reaction mixture thus obtained consists of 1,4-sorbitan, unreacted sorbitol, isosorbide and minor amounts of by-products, as illustrated on the chromatogram shown in FIG. 1. One of the advantages thus observed is the lower level of coloring, this in contrast with the conventional methods of the prior art.

In the following step this reaction mixture is then usable as such, but it is preferable to collect and purify the 1,4-sorbitan from this mixture and to recycle the remainder toward the dehydration step. In a particular embodiment, the 1,4-sorbitan is collected and purified by crystallization. In another preferred embodiment, the 1,4-sorbitan is collected and purified by means of a chromatographic method. This purified 1,4-sorbitan is preferably used as a substrate for the acetalization reaction.

The acetalization reaction is performable with an alkyl aldehyde reagent, wherein the aldehyde reagent contains 5 to 18 carbon atoms. These aldehydes are selectable from linear or branched aldehydes, and from aliphatic or aromatic aldehydes. In a preferred embodiment, the alkyl aldehydes contain 8 to 12 carbon atoms. Some typical representatives of aldehydes are: pentanal, hexanal, heptanal, octanal, nonanal, decanal and dodecanal.

It is also possible to carry out the acetalization using dialkyl acetals of the corresponding aldehydes, with dimethyl acetals and diethyl acetals being preferred.

The acetalization reaction with an aldehyde reagent is executable with or without solvent. When solvent is used, it is selectable from polar solvents such as DMF, DMSO, DMA, acetonitrile, THF, methyl THF and ethyl acetate. Extensive experimental work thus made it possible to select conditions ensuring optimal conversion rates and yields. The best results were obtained when the molar ratio of the substrate to the reagent is between 5:1 and 1:1, preferably between 4:1 and 1:1, and more preferably between 3:1 and 2:1.

When the reaction is carried out without solvent, the 1,4-sorbitan is first heated to between 90 and 110° C., then the aldehyde reagent is added slowly, followed by the addition of the catalyst. The acid catalysts used are selectable from organic or inorganic, solid or liquid acids, with solid acids being preferred. In particular, the preferred acids are selected from para-toluenesulfonic acid, methanesulfonic acid and camphorsulfonic acid (CSA).

In addition, the transacetalization reactions are performable in the presence or in the absence of solvent in order to obtain long-chain alkyl cyclic acetals made from sugars. When solvent is used, it is preferable to use the alcohol corresponding to the acetal reagent used. From experimental work it was noted that in the transacetalization reactions optimal yields and conversion rates were obtained when the molar ratio of the substrate to the reagent is between 1:1 and 1:3, and preferably between 2:3 and 2:5. The same catalysts are used as those used in the acetalization reactions.

During the acetalization reactions, the reaction mixtures are heated to temperatures varying between 70° C. and 100° C., depending on the reagents and solvents used. The reaction time is determined by the degree of conversion reached.

The crude reaction mixtures thus obtained are then treated in order to collect the hexitan alkyl acetals according to the invention. The collection is carried out by separation methods generally known in the state of the art. The typical methods that are usable are, among others, extraction, chromatographic separation and crystallization.

The sorbitan acetal compositions obtained by the methods described above are composed of four diastereoisomers. Two diastereoisomers correspond with a sorbitan 5,6-acetal and the other two correspond to a sorbitan 3,5-acetal. Thus R is a C4-C17 linear aliphatic chain.

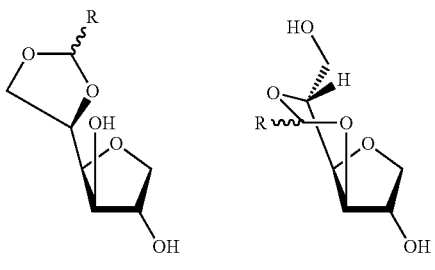

Sorbitan 5,6- and 3,5-acetals

Tests of the stability of the sorbitan alkyl acetal compositions according to the invention were carried out in ethanol and water at various pH values. It was thus noted that less than 1% was hydrolyzed in ethanol after 3 hours at pH 1 and at 80° C.

Tests in water were carried out at three pH values: 7, 5 and 1. At pH=5 and pH=7 no substantial degradation was observed after 48 hours, at temperatures of 20° C. and 40° C. At pH=1, after 4 hours at 20° C., 40% is hydrolyzed, as determined by HPLC. In comparison with the acetals described in JAOCS 1994, p. 705-710, it is clearly better acidic stability compared to these compounds.

The compositions thus obtained are thus usable as non-ionic surfactant, as emulsifier, as lubricant or as dispersant in a wide range of food and non-food applications.

Without limiting the scope of the invention, the invention will now be illustrated in further detail using a certain number of examples describing the methods for preparing these derivatives.

Example 1

Dehydration of Sorbitol

D-Sorbitol (20 g, 110 mmol) and 0.1% (mol/mol) camphorsulfonic acid are added in a 150 ml stainless steel autoclave. The reactor is sealed hermetically, purged with hydrogen three times and then hydrogen was introduced up to a pressure of 50 bar. The system is then heated to 140° C. and shaken with a mechanical shaker for 15 hours. After cooling to room temperature, the hydrogen pressure was released and the white foam was diluted in ethanol (200 ml) in order to obtain a yellow homogeneous mixture. Solvent is evaporated under reduced pressure and the residue is then crystallized from cold methanol and vacuum filtered. The crystalline material was washed with cold methanol to yield 1,4-sorbitan (5.88 g, 35% of theoretical) as a white solid. The purity is >98%, as determined by HPLC, while the crystals exhibited a melting point of 113-114° C. The degree of conversion of the reaction was determined at 73%, whereby is obtained a mixture of sorbitol, 1,4-sorbitan, isosorbide and a few by-products in very limited amounts, such that the ratio of 1,4-sorbitan to isosorbide was determined to be 80:20.

Example 2

Acetalization of Sorbitan in DMF

In a sealed tube, 1,4-sorbitan (X) (0.5 g, 3 mmol) was dissolved in DMF (1.4 ml). Valeraldehyde (Y) (107 μl mmol) was added dropwise under argon followed by the addition of camphorsulfonic acid (10 mg, 10% w/w) before closing the tube. The mixture is heated to 95° C. with magnetic stirring. After 15 hours, the dark reaction mixture was cooled and the solvent evaporated under reduced pressure. A degree of conversion of 95% was reached. The residue was diluted in ethyl acetate and the excess 1,4-sorbitan was filtered and washed with ethyl acetate. The filtrate was concentrated under reduced pressure. The residue is purified by flash chromatography (80:20 to 100:0 EtOAc:cyclohexane) to yield the sorbitan acetal (0.22 g, 89% of isolated yield) as colorless oil. HPLC revealed a mixture of four diastereoisomers.

Example 3

In this example, various ratios of sorbitan versus the aldehyde reagent were tested. The same reaction conditions as in Example 2 were used, but the sorbitan:aldehyde ratio was varied between 1:1 and 3:1. The results are presented in Table 1, below.

TABLE 1

Effect of sorbitan:aldehyde ratio on degree of conversion and isolated yield

| X:Y ratio | Conversion | Isolated yield (wt %) |
|---|---|---|
| 1:1 | 96% | 62% |
| 2:1 | 81% | 83% |
| 3:1 | 95% | 89% |

Example 4

With a sorbitan:aldehyde ratio of 3:1 various aldehyde reagents were used to provide sorbitan acetal reaction products. The same reaction conditions and the same purification steps as in Example 2 were used.

The results are presented in Table 2.

TABLE 2

| Aldehyde | Conversion | Isolated yield |
|---|---|---|
| Hexanal | 100% | 98% |
| Octanal | 89% | 95% |
| Decanal | 69% | 85% |
| Dodecanal | 61% | 80% |

Example 5

In addition to using DMF as solvent, other solvents were also used to prepare the sorbitan acetal compositions. Here also, the same reagents were used and the same procedure was followed as in Example 2, except that the reaction temperatures were around 80° C. The results are presented in Table 3.

TABLE 3

| Solvent | Conversion | Isolated yield |
|---|---|---|
| Acetonitrile | 100% | ND |
| Ethyl acetate | 98% | ND |
| DMF | 83% | 83% |

Example 6

Acetalization of Sorbitan without Solvent

In a sealed tube, 1,4-sorbitan (X) (0.5 g, 3 mmol) was heated to 95° C. Valeraldehyde (Y) (107 µl, 1 mmol) was added dropwise, under argon, then camphorsulfonic acid (10 mg, 10% w/w) before closing the tube again. The mixture is heated to 95° C. with magnetic stirring. After 15 hours, the dark reaction mixture was cooled and diluted in ethyl acetate (2 ml) and the solvent is then evaporated under reduced pressure. A degree of conversion of 80% was obtained. The residue was diluted in ethyl acetate again and the excess 1,4-sorbitan was filtered and washed with ethyl acetate. The filtrate was concentrated under reduced pressure. The residue is purified by flash chromatography (80:20 to 100:0 EtOAc:cyclohexane) to yield the sorbitan acetal (0.13 g, 54% of isolated yield) as colorless oil. HPLC revealed a mixture of four diastereoisomers.

Example 7

Transacetalization of Sorbitan in Ethanol

In a round-bottom flask, 1,4-sorbitan (0.5 g, 3 mmol) was dissolved in ethanol (7.5 ml) and 1,1-diethoxypentane (1.15 ml, 6 mmol) was added under a stream of argon, then camphorsulfonic acid (50 mg, 10% w/w). The mixture is heated to 80° C. with magnetic stirring. After 3 hours, the mixture was neutralized and concentrated under reduced pressure. The residue was purified by flash chromatography (80:20 to 100:0 ethyl acetate/cyclohexane) to yield the sorbitan acetal (0.43 g, 66% of isolated yield) as colorless oil. HPLC revealed a mixture of four diastereoisomers.

Example 8

Transacetalization of Sorbitan without Solvent

Figure 2:
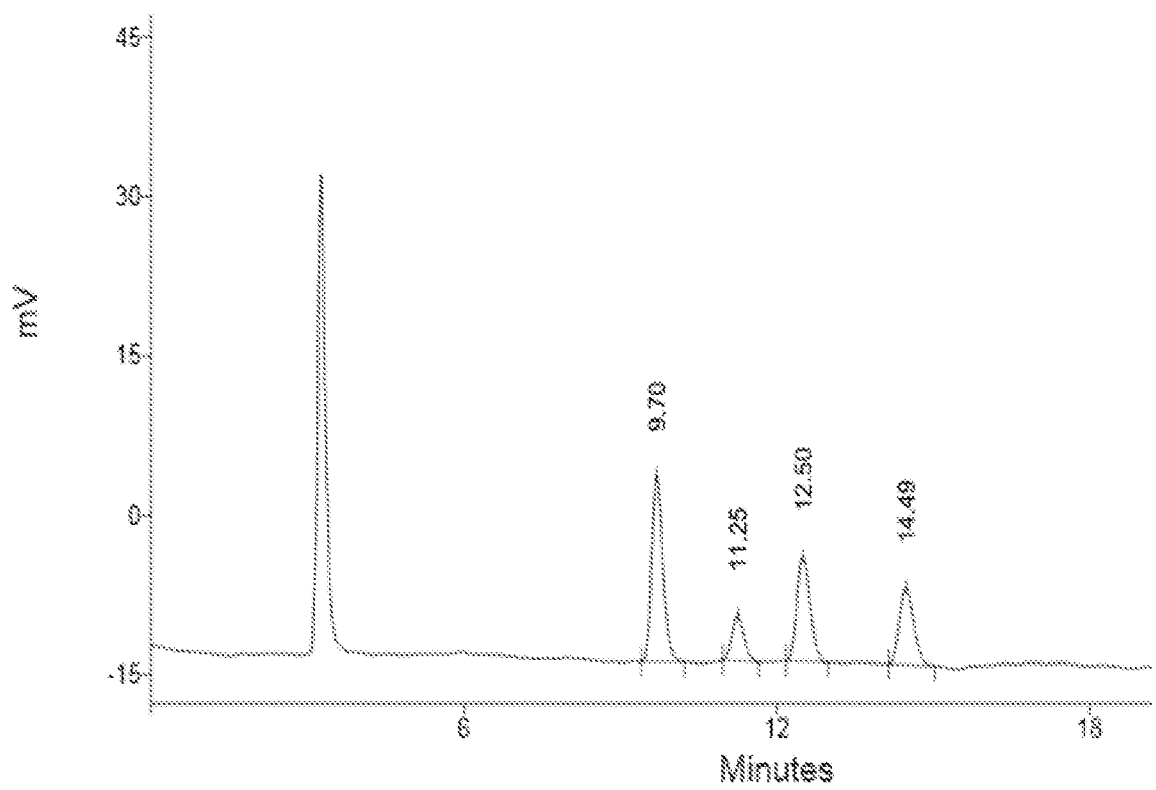
FIG. 2: represents a chromatogram of the reaction mixture obtained by transacetalization without solvent according to Example 8.

In a round-bottom flask, 1,4-sorbitan (0.5 g, 3 mmol) and 1,1-diethoxypentane (1,1-DEP) (1.15 ml, 6 mmol) (1:2 molar ratio) were added under a stream of argon, then camphorsulfonic acid (50 mg, 10% w/w). The mixture is heated to 80° C. with magnetic stirring. After 3 hours, the mixture was purified directly by flash chromatography (80:20 to 100:0 ethyl acetate/cyclohexane) to yield the sorbitan acetal (0.517 g, 73% of isolated yield) as colorless oil. HPLC revealed a mixture of four diastereoisomers (FIG. 2).

Example 9

Transacetalizations without solvent were carried out using various molar ratios, various reagents (1,1-dimethoxypentane), various reaction temperatures and various reaction times, with the catalyst being the same. The reaction mixtures were purified by means of flash chromatography, as in Example 8.

The results are given in Table 4.

TABLE 4

| Reagent | Sorbitan/ reagent ratio | Time (h) | Temperature | Conversion | Isolated yield |
|---|---|---|---|---|---|
| 1,1-DMP | 1:1 | 15 | 70° C. | 99% | 66% |
| 1,1-DEP | 1:1 | 15 | 70° C. | 81% | 66% |
| 1,1-DEP | 1:1 | 15 | 80° C. | — | 49% |
| 1,1-DEP | 1:2 | 3 | 80° C. | 80% | 73% |

The invention claimed is:

1. A method for preparing long-chain alkyl cyclic acetals made from sugars, characterized in that the method comprises the following steps:
   dehydrating a hexitol in a monoanhydrohexitol substrate;
   reacting the monoanhydrohexitol substrate obtained with an alkyl aldehyde reagent containing 5 to 18 carbon atoms, by means of an acetalization reaction with a substrate/reagent ratio of between 5:1 and 1:1, or with a derivative of an alkyl aldehyde reagent containing 5 to 18 carbon atoms, by means of a transacetalization reaction with a substrate/reagent ratio of between 1:1 and 1:3, in the presence of acid catalyst and in an environment that is free of solvent or that consists of non-aqueous polar solvent; and
   collecting the long-chain alkyl acetal of hexitan from the mixture obtained.

2. The method as claimed in claim 1, wherein the hexitol is selected from the group comprising: sorbitol, mannitol, galactitol and iditol.

3. The method as claimed in claim 2, wherein the hexitol is sorbitol.

4. The method as claimed in claim 1, wherein said alkyl aldehyde reagent contains 8 to 12 carbon atoms.

5. The method as claimed in claim 1, wherein said non-aqueous polar solvent is selected from the group consisting of: DMF, DMSO, DMA, acetonitrile, THF, methyl THF and ethyl acetate.

6. The method as claimed in claim 1, wherein the long-chain alkyl acetal of hexitan is collected by separation.

7. The method as claimed in claim 3, wherein said monoanhydrohexitol substrate is purified 1,4-sorbitan.

8. The method as claimed in claim 7, wherein said long-chain alkyl acetal of hexitan is composed of four diastereoisomers.

* * * * *